United States Patent [19]

Petersen et al.

[11] Patent Number: 5,545,642
[45] Date of Patent: Aug. 13, 1996

[54] DERIVATIVES OF 1-(2-FLUOROCYCLOPROPYL)-QUINOLONECARBOXYLIC ACID AND 1-(2-FLUOROCYCLOPROPYL)-NAPHTHRIDONECARBOXYLIC ACID

[75] Inventors: Uwe Petersen, Leverkusen; Thomas Schenke, Bergisch Gladbach; Stefan Böhm, Krefeld; Rolf Grosser, Leverkusen; Klaus D. Bremm, Recklinghausen; Rainer Endermann; Karl G. Metzger, both of Wuppertal, all of Germany

[73] Assignee: Bayer Aktiengesellschaft, Leverkusen, Germany

[21] Appl. No.: 336,638

[22] Filed: Nov. 9, 1994

[30] Foreign Application Priority Data

Nov. 16, 1993 [DE] Germany ............... 43 39 134.6

[51] Int. Cl.$^6$ ............... A61K 31/47; C07D 215/20
[52] U.S. Cl. ............... 514/312; 514/300; 546/123; 546/156
[58] Field of Search ............... 514/312, 300; 546/156, 123

[56] References Cited

U.S. PATENT DOCUMENTS

| | | | |
|---|---|---|---|
| 5,091,384 | 2/1992 | Kim et al. | 514/215 |
| 5,274,167 | 12/1993 | Lange et al. | 560/40 |
| 5,312,823 | 5/1994 | Petersen et al. | 514/300 |

FOREIGN PATENT DOCUMENTS

| | | |
|---|---|---|
| 0391132 | 10/1990 | European Pat. Off. . |
| 0424852 | 5/1991 | European Pat. Off. . |
| 0424850 | 5/1991 | European Pat. Off. . |
| 04248851 | 5/1991 | European Pat. Off. . |
| 0520277 | 12/1992 | European Pat. Off. . |
| 0550016 | 7/1993 | European Pat. Off. . |
| 0593766 | 4/1994 | European Pat. Off. . |
| 0622367 | 11/1994 | European Pat. Off. . |
| 9221659 | 12/1992 | WIPO . |

OTHER PUBLICATIONS

Atarashi, S. Imamura M. Kimura Y. Yoshida A. Hayakawa I. J. Med Chem., vol. 36, pp. 3444–3448 (1993).

*Primary Examiner*—C. Warren Ivy
*Assistant Examiner*—Evelyn Huang
*Attorney, Agent, or Firm*—Sprung Horn Kramer & Woods

[57] ABSTRACT

The invention relates to novel derivatives of 1-(2-fluorocyclopropyl)-quinolonecarboxylic acid and 1-(2-fluorocyclopropyl)-naphthyridonecarboxylic acid which are substituted in the 7 position by a 2,3,4,5,6,7-hexahydro-1H-pyrrolo[3,4-c]pyridin-2-yl or 1,2,3,4,5,6-hexahydropyrrolo[3,4-c]pyrrol-2-yl residue, to their salts, to a process for their preparation and to antibacterial agents containing these derivatives.

12 Claims, No Drawings

DERIVATIVES OF 1-(2-FLUOROCYCLOPROPYL)-QUINOLONECARBOXYLIC ACID AND 1-(2-FLUOROCYCLOPROPYL)-NAPHTHRIDONECARBOXYLIC ACID

The invention relates to novel derivatives of 1-(2-fluorocyclopropyl)-quinolonecarboxylic acid and 1-(2-fluorocyclopropyl)-naphthyridonecarboxylic acid which are substituted in the 7 position by a 2,3,4,5,6,7-hexahydro-1H-pyrrolo[3,4-c]pyridin-2-yl or 1,2,3,4,5,6-hexahydropyrrolo[3,4-c]pyrrol-2-yl residue, to their salts, to a process for their preparation and to antibacterial agents containing these derivatives.

Quinolonecarboxylic acids which carry a 2,3,4,5,6,7-hexahydro-1H-pyrrolo[3,4-c]pyridin-2-yl residue in the 7 position have already been disclosed by the Patent Applications EP 424 850 (Korea Research Institute), EP 424 851 (Korea Research Institute) and EP 520 277 (Bayer). On the other hand, 1-(2-fluorocyclopropyl)quinolonecarboxylic acids have been disclosed by WO 9221659 (Daiichi).

It has now been found that the compounds of the formula (I)

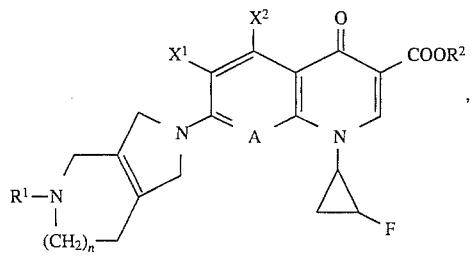

in which $R^1$ represents hydrogen, $C_1$–$C_3$-alkyl which is optionally substituted by hydroxyl, $C_1$–$C_4$-alkoxycarbonyl, acetyl which is optionally substituted by halogen, or (5-methyl-2-oxo-1,3-dioxol-4-yl)-methyl, $R^2$ represents hydrogen, alkyl, having from 1 to 3 carbon atoms, which is optionally substituted by hydroxyl, methoxy, amino, methylamino or dimethylamino, or represents (5-methyl-2-oxo-1,3-dioxol-4-yl)-methyl, acetoxymethyl or pivaloyloxymethyl, n represents 0 or 1, $X^1$ represents halogen or nitro, $X^2$ represents hydrogen, halogen, amino or methyl, A represents N, C—H, C—F, C—Cl, C—Br, C—CF$_3$, C—OCH$_3$, C—OCHF$_2$, C—CH$_3$ or C—C≡CH, and their pharmaceutically utilizable hydrates and acid addition salts, as well as the alkali metal salts, alkaline earth metal salts, silver salts and guanidinium salts of the underlying carboxylic acids, exhibit, while being well tolerated, a high level of antibacterial activity, in particular towards Gram-positive bacteria.

The compounds of the formula (I) are preferred, in which $R^1$ represents hydrogen, methyl, ethyl, t-butoxycarbonyl, acetyl, trifluoroacetyl or trichloroacetyl, $R^2$ represents hydrogen, n represents 0 or 1, $X^1$ represents chlorine or fluorine, $X^2$ represents hydrogen, fluorine, amino or methyl, A represents N, C—K, C—F, C—Cl, C—Br, C—CF$_3$, C—OCH$_3$, C—OCHF$_2$, C—CH$_3$ or C—C≡CH, as are their pharmaceutically utilizable hydrates and acid addition salts, as well as the alkali metal salts, alkaline earth metal salts, silver salts and guanidinium salts of the underlying carboxylic acids.

The compounds of the formula (I) are particularly preferred, in which $R^1$ represents hydrogen or methyl, $R^2$ represents hydrogen, n represents 1, $X^1$ represents fluorine, $X^2$ represents hydrogen, fluorine or amino, A represents N, C—H, C—F, C—Cl, C—Br or C—OCH$_3$, as are their pharmaceutically utilizable hydrates and acid addition salts, as well as the alkali metal salts, alkaline earth metal salts, silver salts and guanidinium salts of the underlying carboxylic acids.

It has furthermore been found that the compounds of the formula (I) are obtained when compounds of the formula (II)

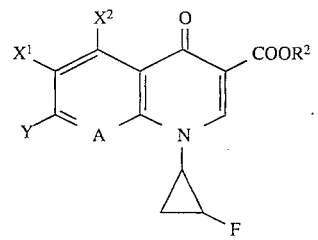

in which $R^2$, $X^1$, $X^2$ and A have the abovementioned meaning, and

Y represents halogen, and in particular represents fluorine or chlorine, are reacted with compounds of the formula (III)

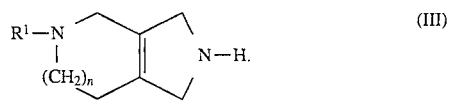

in which $R^1$ and n have the abovementioned meanings, optionally in the presence of acid capturing agents, and any protective groups which may be present are eliminated.

If, for example, 6,7-difluoro-1-(cis-2-fluoro-cyclopropyl)-1,4-dihydro-8-methoxy-4-oxo-3-quinolinecarboxylic acid and 5-tert-butoxycarbonyl-2,3,4,5,6,7-hexahydro-1H-pyrrolo[3,4-c]pyridine are used as starting compounds, the course of the reaction can then be depicted by the following formula scheme:

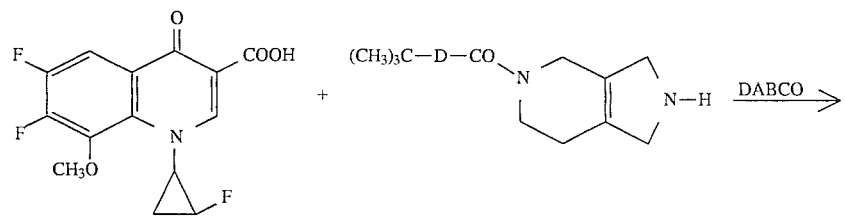

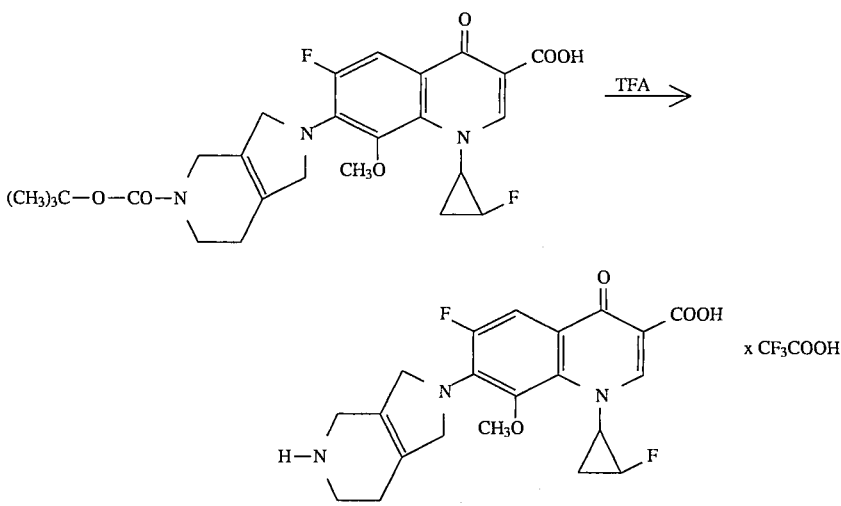

DABCO=1,4-diazabicyclo[2.2.2]octane;
TFA=trifluoroacetic acid

The compounds of the formula (II) used as starting compounds are known or can be prepared by known methods. They may be employed both as racemic and as enantiomerically pure compounds. The following may be mentioned as examples:

8-Bromo-6,7-difluoro-1-(cis-2-fluoro-cyclopropyl)-1,4-dihydro-4-oxo-3-quinolinecarboxylic acid,
8-chloro-6,7-difluoro-1-(cis-2-fluoro-cyclopropyl)-1,4-dihydro-4-oxo-3-quinolinecarboxylic acid,
6,7-difluoro-1-(cis-2-fluoro-cyclopropyl)-1,4-dihydro-4-oxo-3-quinolinecarboxylic acid,
6,7,8-trifluoro-1- (cis-2-fluoro-cyclopropyl) -1,4-dihydro-4-oxo-3-quinolinecarboxylic acid,
5,6,7,8-tetrafluoro-1-(cis-2-fluoro-cyclopropyl)-1,4-dihydro-4-oxo-3-quinolinecarboxylic acid,
6,7-difluoro-1-(cis-2-fluoro-cyclopropyl)-1,4-dihydro-8-methyl-4-oxo-3-quinolinecarboxylic acid,
8-ethinyl-6,7-difluoro-1-(cis-2-fluoro-cyclopropyl)-1,4-dihydro-4-oxo-3-quinolinecarboxylic acid,
6,7-difluoro-1-(cis-2-fluoro-cyclopropyl)-1,4-dihydro-4-oxo-8-trifluoromethyl-3-quinolinecarboxylic acid,
6,7-difluoro-1-(cis-2-fluoro-cyclopropyl)-8-difluoromethoxy-1,4-dihydro-4-oxo-3-quinolinecarboxylic acid,
6,7-difluoro-1-(cis-2-fluoro-cyclopropyl)-1,4-dihydro-8-methoxy-4-oxo-3-quinolinecarboxylic acid,
6,7-difluoro-1-(cis-2-fluoro-cyclopropyl)-1,4-dihydro-5-methyl-4-oxo-3-quinolinecarboxylic acid,
5-amino-6,7,8-trifluoro-1-(cis-2-fluoro-cyclopropyl)-1,4-dihydro-4-oxo-3-quinolinecarboxylic acid,
8-bromo-6,7-difluoro-1-(trans-2-fluoro-cyclopropyl)-1,4-dihydro-4-oxo-3-quinolinecarboxylic acid,
8-chloro-6,7-difluoro-1-(trans-2-fluoro-cyclopropyl)-1,4-dihydro-4-oxo-3-quinolinecarboxylic acid,
6,7-difluoro-1-(trans-2-fluoro-cyclopropyl)-1,4-dihydro-4-oxo-3-quinolinecarboxylic acid,
6,7,8-trifluoro-1- ( trans-2-fluoro-cyclopropyl)-1,4-dihydro-4-oxo-3-quinolinecarboxylic acid,
5,6,7,8-tetrafluoro-1-(trans-2-fluoro-cyclopropyl)-1,4-dihydro-4-oxo-3-quinolinecarboxylic acid,
6,7-difluoro-1-(trans-2-fluoro-cyclopropyl)-1,4-dihydro-8-methyl-4-oxo-3-quinolinecarboxylic acid,
8-ethinyl-6,7-difluoro-1-(trans-2-fluoro-cyclopropyl)-1,4-dihydro-4-oxo-3-quinolinecarboxylic acid,
6,7-difluoro-1-(trans-2-fluoro-cyclopropyl)-1,4-dihydro-4-oxo-8-trifluoromethyl-3-quinolinecarboxylic acid,
6,7-difluoro-1-(trans-2-fluoro-cyclopropyl)-8-difluoromethoxy-1,4-dihydro-4-oxo-3-quinolinecarboxylic acid,
6,7-difluoro-1-(trans-2-fluoro-cyclopropyl)-1,4-dihydro-8-methoxy-4-oxo-3-quinolinecarboxylic acid,
6,7-difluoro-1-(trans-2-fluoro-cyclopropyl)-1,4-dihydro-5-methyl-4-oxo-3-quinolinecarboxylic acid,
5-amino-6,7,8-trifluoro-1-(trans-2-fluoro-cyclopropyl)-1,4-dihydro-4-oxo-3-quinolinecarboxylic acid.

The enantiomerically pure starting compounds of the formula (II) can be prepared by starting from enantiomerically pure 2-fluorocyclopropylamines. However, the racemic compounds of the formula (II) can also be reacted with enantiomerically pure bases to form a mixture of the diastereomeric salts which can be separated by fractional crystallization into the diastereomerically pure salts, from which the enantiomerically pure compounds of the formula (II) can be liberated by treatment with suitable acids, for example mineral acids such as hydrochloric acid or sulphuric acid.

However, the racemic compounds of the formula (II) can also be advantageously separated by chromatography on chiral separating materials. These materials preferably include optically active polymers of optically active derivatives of (meth)-acrylic acid. In this context, polymers of optically active N-(meth)-acryloyl amino acid derivatives, as described in European Patent Application 379 917, are particularly preferred. In this context, polymers of the following optically active N-acryloyl amino acid esters may be mentioned as being very particularly preferred: N-acryloyl-L-amino acid menthyl ester or N-acryloyl-D-amino acid menthyl ester, with examples of suitable amino acids being leucine, alanine, phenylalanine, valine or other amino acids.

Customary organic solvents or solvent mixtures which cause the polymer used as adsorbent to swell and dissolve the racemate to be resolved are used as the mobile phase for resolving the racemate. Examples which may be mentioned are: hydrocarbons, such as benzene, toluene or xylene, ethers, such as diethyl ether, dioxane or tetrahydrofuran, halogenohydrocarbons, such as dichloromethane or trichloromethane, acetone, acetonitrile or ethyl acetate, or else mixtures of the said solvents. Mixtures of toluene and tetrahydrofuran and mixtures of toluene and dioxane have been found to be particularly suitable.

Some of the bicyclic amines of the formula (III) which are required as starting compounds are known. The following may be mentioned as examples:

2,3,4,5,6,7-Hexahydro-1H-pyrrolo[3,4-c]pyridine,
5-ethyl-2,3,4,5,6,7-hexahydro-1H-pyrrolo[3,4-c]pyridine,
5-methyl-2,3,4,5,6,7-hexahydro-1H-pyrrolo[3,4-c]pyridine,
5-(2-hydroxyethyl)-2,3,4,5,6,7-hexahydro-1H-pyrrolo [3,4c]pyridine,
5-tert-butoxycarbonyl-2,3,4,5,6,7-hexahydro-1H-pyrrolo[3, 4-c ]pyridine,
5-trifluoroacetyl-2,3,4,5,6,7-hexahydro-1H-pyrrolo[3,4c] pyridine,
hexahydro-pyrrolo[3,4-c]pyrrole,
2-methyl-hexahydro-pyrrolo[3,4-c]pyrrole,
2-ethyl-hexahydro-pyrrolo[3,4-c]pyrrole.

The reaction of (II) with (III), in which the compounds (III) may also be employed in the form of their salts, such as, for example, the hydrochlorides, is preferably carried out in a diluent, such as dimethyl sulphoxide, N,N-dimethylformamide, N-methylpyrrolidone, hexamethylphosphoric triamide, sulpholane, acetonitrile, water, an alcohol, such as methanol, ethanol, n-propanol or isopropanol, glycol monomethyl ether or pyridine. Mixtures of these diluents may also be used.

All the customary inorganic and organic acid binding agents can be used as acid binders. These agents preferably include the alkali metal hydroxides, alkali metal carbonates, organic amines and amidines. The following may be specifically mentioned as being particularly suitable: triethylamine, 1,4-diazabicyclo[2.2.2]octane (DABCO), 1,8-diazabicyclo[5.4.0]undec-7-ene (DBU) or excess amine (III).

The reaction temperatures may be varied within a relatively wide range. In general, temperatures of between about 20° and 200° C., preferably of between 80° and 160° C., are employed.

While the reaction can be carried out under atmospheric pressure, it can also be carried out under elevated pressure. In general, pressures of between about 1 and 100 bar, preferably of between 1 and 10 bar, are employed.

In carrying out the process according to the invention, from 1 to 15 mol, preferably from 1 to 5 mol, of the compound (III) are employed per 1 mol of the compound (II).

Free amino groups can be protected during the reaction by means of a suitable amino protection group, such as, for example, by means of the tert-butoxycarbonyl radical, and liberated once more when the reaction is complete.

In order to prepare the esters according to the invention, the underlying carboxylic acid is preferably reacted in excess alcohol in the presence of strong acids, such as sulphuric acid, anhydrous hydrogen chloride, methanesulphonic acid or p-toluenesulphonic acid, or acidic ion exchangers, at temperatures of from about 20° to 180° C., preferably of from about 60° to 120° C. The water of reaction which arises can also be removed by azeotropic distillation with chloroform, tetrachloromethane or toluene.

The esters are also advantageously prepared by heating the underlying acid with dimethylformamide dialkyl acetal in a solvent such as dimethylformamide.

The 5-methyl-2-oxo-1, 3-dioxol-4-yl-methyl esters used as prodrugs are obtained by reacting an alkali metal salt of the underlying carboxylic acid, which, if appropriate, can be protected on the N atom by a protective group such as the tert-butoxycarbonyl radical, with 4-bromomethyl-5-methyl-1,3-dioxol-2-one or 4-chloromethyl-5-methyl-1,3-dioxol-2-one in a solvent such as dimethylformamide, dimethylacetamide, N-methyl-pyrrolidone, dimethyl sulphoxide or tetramethylurea at temperatures of from about 0° to 100° C., preferably from 0° to 50° C. The acid addition salts of the compounds according to the invention are prepared in a customary manner, for example by dissolving in excess aqueous acid and precipitating the salt with a solvent, such as methanol, ethanol, acetone or acetonitrile, which is miscible with water. Equivalent quantities of betaine and acid can also be heated in water or an alcohol such as glycol monomethyl ether and the mixture subsequently evaporated to dryness or the precipitated salt filtered off with suction. Pharmaceutically utilizable salts are understood, for example, to be the salts of hydrochloric acid, sulphuric acid, acetic acid, glycolic acid, lactic acid, succinic acid, citric acid, tartaric acid, 2-hydroxyglutaric acid, methanesulphonic acid, 4-toluenesulphonic acid, galacturonic acid, glucuronic acid, 5-oxotetrahydrofuran-2-carboxylic acid, embonic acid, glutamic acid or aspartic acid.

The alkali metal salts and alkaline earth metal salts of the carboxylic acids according to the invention are obtained, for example, by dissolving the betaine in excess alkali metal hydroxide solution or alkaline earth metal hydroxide solution, removing the undissolved betaine by filtration and evaporating the filtrate to dryness. Sodium, potassium and calcium salts are pharmaceutically suitable. The corresponding silver salts are obtained by reacting an alkali metal salt or alkaline earth metal salt with a suitable silver salt such as silver nitrate.

The active compounds listed in the following table, which can be present as racemates or as enantiomerically pure compounds or, where appropriate, also as diastereomeric mixtures or as diastereomerically pure compounds, can also be prepared in addition to the active compounds specified in the examples:

| $R^1$ | n | $X^2$ | A |
|---|---|---|---|
| $CH_3$ | 1 | $NH_2$ | N |
| $CH_3$ | 1 | H | $C-OCHF_2$ |
| $CH_3$ | 1 | H | $C-Br$ |
| $CH_3$ | 1 | H | $C-CF_3$ |
| $CH_3$ | 1 | H | $C-OCH_3$ |
| $CH_3$ | 1 | H | $C-CH_3$ |
| $CH_3$ | 1 | H | $C-C\equiv CH$ |
| $CH_3$ | 1 | F | $C-F$ |
| $CH_3$ | 1 | $NH_2$ | $C-F$ |
| $CH_3$ | 1 | $CH_3$ | $C-F$ |
| $CH_3$ | 1 | $CH_3$ | H |
| H | 1 | H | N |
| H | 1 | H | $C-H$ |
| H | 1 | H | $C-F$ |
| H | 1 | H | $C-Cl$ |
| H | 1 | H | $C-CBr$ |
| H | 1 | H | $C-CF_3$ |
| H | 1 | H | $C-OCH_3$ |
| H | 1 | H | $C-OCHF_2$ |
| H | 1 | H | $C-CH_3$ |
| H | 1 | H | $C-C\equiv CH$ |

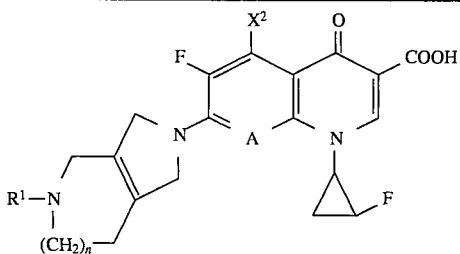

| R¹ | n | X² | A |
|---|---|---|---|
| H | 1 | F | C—F |
| H | 1 | NH₂ | C—F |
| H | 1 | CH₃ | C—F |
| H | 1 | CH₃ | C—H |
| H | 0 | H | N |
| H | 0 | H | C—H |
| H | 0 | H | C—F |
| H | 0 | H | C—Cl |
| H | 0 | H | C—Br |
| H | 0 | H | C—OCH₃ |
| H | 0 | H | C—OCHF₂ |
| H | 0 | H | C—CH₃ |
| H | 0 | H | C—C≡CH |
| CH₃ | 0 | H | N |
| CH₃ | 0 | H | C—H |
| CH₃ | 0 | H | C—F |
| CH₃ | 0 | H | C—Cl |
| CH₃ | 0 | H | C—Br |
| CH₃ | 0 | H | C—OCH₃ |
| CH₃ | 0 | H | C—OCHF₂ |
| CH₃ | 0 | H | C—CH₃ |
| CH₃ | 0 | H | C—C≡CH |
| HO—CH₂CH₂ | 0 | H | C—F |
| HO—CH₂CH₂ | 0 | H | C—Cl |
| HO—CH₂CH₂ | 0 | H | C—H |
| HO—CH₂CH₂ | 1 | H | C—F |
| HO—CH₂CH₂ | 1 | H | C—Cl |

| R¹ | R² | n | X¹ | X² | A |
|---|---|---|---|---|---|
| H | H | 0 | Cl | H | C—H |
| H | H | 0 | Cl | H | C—F |
| H | H | 1 | Cl | H | N |
| H | C₂H₅ | 0 | F | H | C—F |
| H | C₂H₅ | 1 | F | H | C—F |
| H | C₂H₅ | 1 | F | H | C—OCH₃ |
| H | H | 0 | NO₂ | H | C—F |
| H | C₂H₅ | 0 | F | NH₂ | C—F |
| H | HO—CH₂CH₂ | 0 | F | H | C—F |
| H | H | 0 | F | F | C—F |
| CH₃ | (CH₃)₂N—CH₂CH₂ | 1 | F | H | C—F |
| CH₃ | H | 1 | Cl | H | C—H |
| CH₃ | H | 0 | Cl | H | C—F |
| CH₃ | C₂H₅ | 0 | F | F | C—OCH₃ |
| CH₃ | C₂H₅ | 0 | F | H | C—Cl |
| CH₃ | CH₃ | 0 | F | H | C—OCH₃ |

The compounds according to the invention have a strong antibiotic effect and, while being of low toxicity, exhibit a broad antibacterial spectrum towards Gram-positive and Gram-negative organisms, also and in particular towards those which are resistant to a variety of antibiotics, such as, for example, penicillins, cephalosporins, aminoglycosides, sulphonamides and tetracyclines, as well as to commercially available quinolones.

These valuable properties permit their use as chemotherapeutic active compounds in medicine and as substances for preserving inorganic and organic materials, for example polymers, lubricants, paints, fibres, leather, paper and wood, as well as foodstuffs and water.

The compounds according to the invention are active against a very broad spectrum of microorganisms. Using these compounds, Gram-negative and Gram-positive bacteria and bacterium-like microorganisms can be controlled and the diseases elicited by these pathogens prevented, alleviated and/or cured.

The compounds according to the invention are notable for an amplified effect on resting organisms. The compounds have a strong bactericidal effect on resting bacteria, that is bacteria which do not exhibit any detectable growth. This bactericidal effect relates not only to the quantity of the compounds to be employed but also to the speed at which the microorganisms are destroyed. Results of this nature were observed with Gram-positive and Gram-negative bacteria, in particular with *Staphylococcus aureus, Pseudomonas aeruginosa, Enterococcus faecalis* and *Escherichia coli*.

The compounds according to the invention are particularly active against typical and a typical *mycobacteria* and *Helicobacter pylori* as well as against bacterium-like microorganisms, such as, for example, *mycoplasmas* and *rickettsias*. They are therefore particularly well suited for use in human and veterinary medicine for the prophylaxis and chemotherapy of local and systemic infections which are caused by these pathogens.

In addition to this, the compounds are particularly suitable for controlling protozoal diseases and helminthiases.

The compounds according to the invention may be employed in a variety of pharmaceutical preparations. Tablets, coated tablets, capsules, pills, granules, suppositories, solutions, suspensions and emulsions, pastes, ointments, gels, creams, lotions, powders and sprays may be mentioned as preferred pharmaceutical preparations.

The compounds according to the invention can also be linked to β-lactam derivatives, such as, for example, cephalosporins or penems, via covalent bonds to form so-called dual-action derivatives.

The minimum inhibitory concentrations (MIC) were determined on Iso-Sensitest agar (Oxoid) using a serial dilution method. For each substance to be tested, a series of agar plates was prepared, which plates contained diminishing concentrations of the active compound produced in each case by a doubling dilution. The agar plates were inoculated using a Multipoint Inoculator (Denley). For the inoculation, overnight cultures of the pathogens were used which had been diluted beforehand such that each inoculation point contained approximately 10⁴ colony-forming particles. The inoculated agar plates were incubated at 37° C. and the growth of organisms recorded after about 20 hours. The MIC value (μg/ml) indicates the lowest concentration of active compound at which no growth was visible to the naked eye.

In Table 1, the MIC values for some of the compounds according to the invention are compared with 1-cyclopropyl-6,8-difluoro-1,4-dihydro-7-(5-methyl-2,3,4,5,6,7-hexahydro-1H-pyrrolo[3,4-c]pyridin-2-yl)-4-oxo-3-quinolinecarboxylic acid hydrochloride (ref. 1: Example 7 B from European Patent Application 520 277) and 8-chloro-1-cyclopropyl-6-fluoro-1,4-dihydro-7-(5-methyl-2,3,4,5,6,7-hexahydro-1H-pyrrolo[3,4-c]pyridin-2-yl)-4-oxo-3-quino-1-linecarboxylic acid (ref. 2: Example 8 from European Patent Application 520 277):

TABLE 1

| | | MIC values (μg/ml) | | | | | |
| | | Example | | | | | |
| Species | Strain | 1 | 2 | 3 | 4 | Ref. 1 | Ref. 2 |
| --- | --- | --- | --- | --- | --- | --- | --- |
| *Escherichia coli* | Neumann | ≦0.015 | 0.03 | ≦0.015 | ≦0.015 | ≦0.015 | 0.03 |
| *Klebsiella* sp. | 8085 | 0.06 | 0.06 | 0.06 | 0.06 | 0.06 | 0.06 |
| *Morganella morganii* | 932 | 0.03 | 0.06 | 0.06 | 0.06 | 0.03 | 0.06 |
| *Providencia* sp. | 12012 | 0.06 | 0.06 | 0.06 | 0.06 | 0.125 | 0.125 |
| *Micrococcus luteus* | 9341 | 0.25 | 0.25 | 0.125 | 0.125 | 0.5 | 0.25 |
| *Staphylococcus aureus* | ICB 25701 | 0.5 | 0.5 | 0.5 | 0.25 | 1 | 0.5 |
| | 133 | 0.06 | 0.06 | 0.06 | ≦0.015 | 0.6 | 0.03 |
| *Enterococcus faecalis* | 27101 | 0.06 | 0.06 | 0.06 | 0.06 | 0.125 | 0.06 |

The compounds according to the invention are particularly notable for the fact that they possess improved short-term tolerance and exhibit less interaction with mammalian DNA as compared with the state of the art compounds. The results are depicted in Table 2. The $LD_{50}$ values listed in this table were determined following intravenous administration of the substances to CFl mice. The $ID_{50}$ is understood to be the concentration of a substance at which the DNA synthesis in Chinese hamster ovary cells (CHO-KI) is inhibited by 50%. This value is determined following incubation of the corresponding substances in descending dilution steps for defined periods. For this purpose, the DNA synthesis in CHO-KI cells is determined in comparison to controls using fluorophotometric methods.

TABLE 2

| | Tolerance parameters | | | | |
| | Example | | | | |
| | 1 | 2 | 3 | Ref. 1 | Ref. 2 |
| --- | --- | --- | --- | --- | --- |
| $LD_{50}$ (mg/kg) | 150 | 200 | 50 | 50 | 50 |
| $ID_{50}$ (μg/ml) | 35 | 40 | 40 | 1 | 16 |

Preparation of the intermediates

EXAMPLE I 1

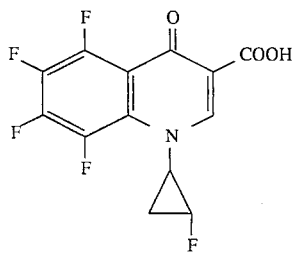

A. While cooling with ice, 1.3 g (11.6 mmol) of 1,4-diazabicyclo[2.2.2]octane are added to a suspension of 2.5 g (22 mmol) of racemic trans-2-fluorocyclopropylamine hydrochloride in 10 ml of acetic acid, and a solution of 7 g (approximately 20 mmol) of ethyl 3-dimethylamino-2-(pentafluorobenzoyl)acrylate in 8 ml of acetic acid are then added dropwise within the space of 10 minutes. The mixture is subsequently left stirring, without cooling, for 4 hours and is then concentrated at 70° C./15 mbar; the residue is taken up in 25 ml of dichloromethane and this solution is washed with water, dried with sodium sulphate and concentrated once again, and the residue is purified by chromatography on 200 g of silica gel using dichloromethane as the eluent. An oil is isolated which slowly crystallizes thoroughly.

Yield: 2.1 g (27.5% of theory) of ethyl 3-(trans-2-fluorocyclopropylamino)-2-(pentafluorobenzoyl)acrylate, melting point: 103°–105° C.

B. 250 mg (6 mmol) of sodium fluoride are added to 2 g (5.4 mmol) of ethyl 3-(trans-2-fluoro-cyclopropylamino)-2-(pentafluorobenzoyl)-acrylate in 10 ml of dimethylformamide, and the mixture is heated under reflux for 2 hours. After having been cooled down, the suspension is introduced into 50 ml of ice water and the undissolved residue is filtered off with suction, washed with water and dried at 80° C. under a high vacuum.

Yield: 1.4 g (74% of theory) of ethyl 5,6,7,8-tetrafluoro-1-(trans-2-fluoro-cyclopropyl)-1,4-dihydro-4-oxo-3-quinolinecarboxylate, melting point: 135°–138° C. (with decomposition).

C. 1.35 g (3.9 mmol) of ethyl 5,6,7,8-tetrafluoro-1-(trans-2-fluoro-cyclopropyl)-1,4-dihydro-4-oxo-3quinolinecarboxylate are heated under reflux for 2 hours in a mixture of 6.3 ml of acetic acid, 4.2 ml of water and 0.64 ml of concentrated sulphuric acid. After having been cooled down, this mixture is introduced into 40 ml of ice water and the undissolved precipitate is filtered off, washed with water and dried at 110° C. under high vacuum. Yield: 0.9 g (72% of theory) of 5,6,7,8-tetrafluoro-1-(trans-2-fluorocyclopropyl)-1,4-dihydro-4-oxo-3-quinolinecarboxylic acid, melting point: 184°–186° C. (with decomposition). 5,6,7,8-Tetrafluoro-1-(cis-2-fluoro-cyclopropyl)-1,4-dihydro-4-oxo-3-quinolinecarboxylic acid is prepared in an analogous manner.

Example I 2

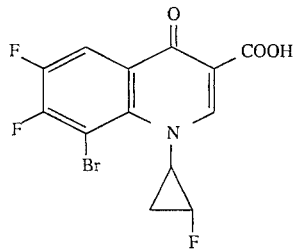

A. 2.2 g (20 mmol) of trans-2-fluoro-cyclopropylamine hydrochloride and 1.2 g (10.7 mmol) of 1,4-diazabicyclo[2.2.2]octane are added to a solution of 7.6 g (20 mmol) of ethyl 2-(3-bromo-2,4,5-trifluorobenzoyl)-3-ethoxyacrylate in 30 ml of ethanol, and the mixture is stirred at room temperature overnight. The precipitate which has been deposited is filtered off with suction, treated with 40 ml of water and dried.

Yield: 5.9 g (72% of theory) of ethyl 2-(3-bromo-2,4,5-trifluoro-benzoyl)-3-(trans-2-fluoro-cyclopropylamino)-acrylate, melting point: 99°–100° C.

5,6,7,8-Tetrafluoro-1-(cis-2-fluoro-cyclopropyl)-1,4-dihydro-4-oxo-3-quinolinecarboxylic acid is prepared in an analogous manner.

Example I 2

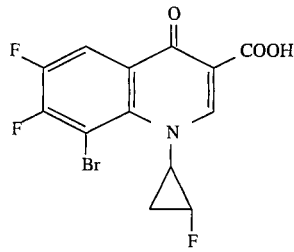

A. 2.2 g (20 mmol) of trans-2-fluoro-cyclopropylamine hydrochloride and 1.2 g (10.7 mmol) of 1,4-diazabicyclo[2.2.2]octane are added to a solution of 7.6 g (20 mmol) of ethyl 2-(3-bromo-2,4,5-trifluorobenzoyl)-3-ethoxyacrylate in 30 ml of ethanol, and the mixture is stirred at room temperature overnight. The precipitate which has been deposited is filtered off with suction, treated with 40 ml of water and dried.

Yield: 5.9 g (72% of theory) of ethyl 2-(3-bromo-2,4,5-trifluoro-benzoyl)-3-(trans-2-fluoro-cyclopropylamino)-acrylate, melting point: 99°–100° C.

B. 5.8 g (14 mmol) of ethyl 2-(3-bromo-2,4,5-trifluorobenzoyl)-3-(trans-2-fluoro-cyclopropylamino)acrylate are heated under reflux for 2 hours in 25 ml of dimethylformamide together with 1.1 g (26 mmol) of sodium fluoride. The suspension is introduced into 100 ml of ice water and the mixture is stirred for 30 minutes and filtered with suction. The precipitate is washed with water and dried at 100° C. under high vacuum.

Yield: 5.1 g (92.7% of theory) of ethyl 8-bromo-6,7-difluoro-1-(trans-2-fluorocyclopropyl)-1,4-dihydro-4-oxo-3-quinolinecarboxylate, melting point: 172°–174° C. (with decomposition).

C. 2.5 ml of concentrated sulphuric acid are added to 5.1 g (13 mmol) of ethyl 8-bromo-6,7-difluoro-1-(trans-2-fluoro-cyclopropyl)-1,4-dihydro-4-oxo-3-quinolinecarboxylate in a mixture of 23 ml of acetic acid and 15 ml of water. This mixture is heated under reflux for 2 hours, with the mixture firstly going into solution and the acid then precipitating out after about 30 minutes. The mixture is introduced into 200 ml of ice water, and the precipitate is filtered off with suction and washed with water and dried at 100° C. under high vacuum.

Yield: 4.3 g (96% of theory) of 8-bromo-6,7-difluoro-1-(trans-2-fluorocyclopropyl)-1,4-dihydro-4-oxo-3-quinolinecarboxylic acid, melting point: 224°–225° C. (with decomposition) (from glycol monomethyl ether), $^1$H-NMR (DMSO): δ 8.8 s (1 H), 8.3 ppm dd (1H).

8-Bromo-6,7-difluoro-1-(cis-2-fluoro-cyclopropyl)-1,4-dihydro-4-oxo-3-quinolinecarboxylic acid is prepared in an analogous manner.

Example I 3

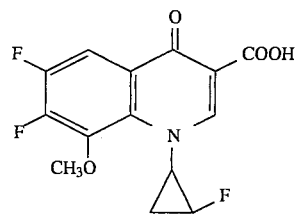

A. While cooling with ice, 325 mg (2.9 mmol) of 1,4-diazabicyclo[2.2.2]octane are added to a suspension of 613 mg (5.5 mmol) of racemic cis-2-fluoro-cyclopropylamine hydrochloride in 2.5 ml of acetic acid, and a solution of 1.66 g (5 mmol) of ethyl 3-ethoxy-2-(2,4,5-trifluoro-3-methoxy-benzoyl)-acrylate in 2 ml of acetic acid is added dropwise. The mixture is left stirring, without cooling, for 4 hours and is then heated at 50° C. for a further 1 hour; the suspension is concentrated and the residue is stirred up with about 15 ml of water. The precipitate is filtered off with suction, washed with water and dried.

Yield: 1.3 g (72% of theory) of ethyl 3-(cis-2-fluoro-cyclopropylamino)-2-(2,4,5-trifluoro-3-methoxy-benzoyl)-acrylate, melting point: 82°–83° C.

B. 160 mg of sodium hydride (97% strength) are added to 1.3 g (3.6 mmol) of ethyl 3-(cis-2-fluoro-cyclopropylamino)-2-(2,4,5-trifluoro-3-methoxy-benzoyl)acrylate in 30 ml of anhydrous tetrahydrofuran, and the mixture is stirred at room temperature for 1 hour. The mixture is then stirred up with 10 ml of 1N hydrochloric acid, concentrated somewhat and extracted with approximately 50 ml of ethyl acetate. The organic phase is separated off, washed with water, dried with sodium sulphate and concentrated. The greasy residue is stirred up with approximately 20 ml of diethyl ether and the crystalline crop which is precipitated is filtered off with suction and dried.

Yield: 814 mg (66% of theory) of ethyl 6,7-difluoro-1-(cis-2-fluoro-cyclopropyl)-1,4-dihydro-8-methoxy-4-oxo-3-quinolinecarboxylate, melting point: 140°–142° C.

C. 610 mg (1.8 mmol) of ethyl 6,7-difluoro-1-(cis-2-fluoro-cyclopropyl)-1,4-dihydro-8-methoxy-4-oxo-3-quinolinecarboxylate are hydrolysed at 150° C. for 2 hours in a mixture of 3.5 ml of acetic acid, 2.4 ml of water and 0.4 ml of concentrated sulphuric acid. The suspension is poured onto ice and thoroughly stirred up, and the precipitate is filtered off with suction, washed with water and approximately 5 ml of methanol, and dried at 60° C. under high vacuum.

Yield: 519 mg (93% of theory) of 6,7-difluoro-1-(cis-2-fluoro-cyclopropyl)-1,4-dihydro-8-methoxy-4-oxo-3-quinolinecarboxylic acid, melting point: 180°–182° C. (with decomposition), remains unchanged after recrystallization from glycol monomethyl ether.

$^1$H-NMR (DMSO): δ 8.8 s (1 H), 8.0 dd (1 H), 5.25 dm and 4.95 ppm dm (together 1 H: CH-F).

Example I 4

Enantiomeric resolution of 6,7,8-trifluoro-1-(cis-2-fluoro-cyclopropyl)-1,4-dihydro-4-oxo-3-quinolinecarboxylic acid: A solution of 1 g of 6,7,8-trifluoro-1-(cis-2-fluoro-cyclopropyl)-1,4-dihydro-4-oxo-3-quinolinecarboxylic acid in 100 g of tetrahydrofuran and 150 ml of toluene is loaded onto a chromatography column (bed height: 350 mm; diameter: 120 mm) containing a bead polymer of N-(acryloyl)-L-phenylalanine-D-menthyl ester (see European Patent Application 379 917) as the stationary phase. Elution is carried out using toluene/tetrahydrofuran 5:1 (v:v) at a flow rate of 8 ml/min. A flow-through photometer (detection wavelength 290 nm) is used for the detection. After about 8 hours, elution of the first enantiomer begins. The fractionated eluates are combined following analytical monitoring for enantiomeric purity. 0.4 g of each of the two enantiomers is obtained once the solvent has been evaporated off.

The enantioselectivity value ($\alpha$ value) using this separating material under analytical conditions (column: 270 mm ×12.5 mm; eluent: toluene/tetrahydrofuran (10/1 v/v); flow rate: 0.5 ml/min; detection wavelength: 290 nm) is $\alpha=2.16$.

Example I 5

Enantiomeric resolutions can also be carried out, in analogy with Example I 4, on appropriate silica gel phases which have been coated with polymers (see European Patent Application 379 917): Cole: 250 mm ×4.6 mm; eluent: n-heptane/THF (3/2 v/v); flow rate: 1 ml/min; detection wavelength: 280 nm. The following enantioselectivity values ($\alpha$ values) are measured under these conditions:
6,7,8-Trifluoro-1-(cis-2-fluoro-cyclopropyl)-1,4-dihydro-4-oxo-3-quinolinecarboxylic acid ($\alpha$ value: 1.98),
6,7,8-trifluoro-1-(trans-2-fluoro-cyclopropyl)-1,4-dihydro-4-oxo-3-quinolinecarboxylic acid($\alpha$ value: 1.00),
5,6,7,8-tetrafluoro-1-(trans-2-fluoro-cyclopropyl)-1,4-dihydro-4-oxo-3-quinolinecarboxylic acid ($\alpha$ value: 1.13),
8-chloro-6,7-difluoro-1-(cis-2-fluoro-cyclopropyl)-1,4-dihydro-4-oxo-3-quinolinecarboxylic acid($\alpha$ value: 1.11),
8-chloro-6,7-difluoro-1-(trans-2-fluoro-cyclopropyl)-1,4-dihydro-4-oxo-3-quinolinecarboxylic acid($\alpha$ value: 1.21),
6,7-difluoro-1-(cis-2-fluoro-cyclopropyl)-1,4-dihydro-4-oxo-3-quinolinecarboxylic acid ($\alpha$ value: 2.55),
6,7-difluoro-1-(trans-2-fluoro-cyclopropyl)-1,4-dihydro-4-oxo-3-quinolinecarboxylic acid ($\alpha$ value: 1.08),
7-chloro-6-fluoro-1-(cis-2-fluoro-cyclopropyl)-1,4-dihydro-4-oxo-1,8-naphthyridine-3-carboxylic acid ($\alpha$ value: 2.28),
7-chloro-6-fluoro-1-(trans-2-fluoro-cyclopropyl)-1,4-dihydro-4-oxo-1,8-naphthyridine-3-carboxylic acid ($\alpha$ value: 1.07),
8-bromo-6,7-difluoro-1-(trans-2-fluoro-cyclopropyl)-1,4-dihydro-4-oxo-3-quinolinecarboxylic acid ($\alpha$ value: 1.11),
6,7-difluoro-1-(cis-2-fluoro-cyclopropyl)-1,4-dihydro-8-methoxy-4-oxo-3-quinolinecarboxylic acid ($\alpha$ value: 1.71).

Preparation of the Active Compounds

EXAMPLE 1

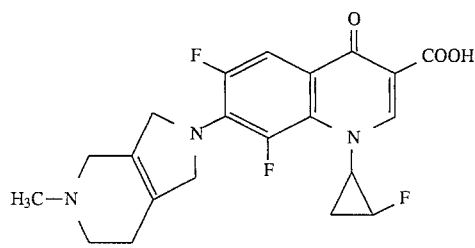

3.0 g (10 mmol) of 6,7,8-trifluoro-1-(cis-2-fluorocyclopropyl)-1,4-dihydro-4-oxo-3-quinolinecarboxylic acid are heated under reflux for 1 hour in a mixture of 40 ml of acetonitrile and 20 ml of dimethylformamide together with 1.25 g (11 mmol) of 1,4-diazabicyclo[2.2.2]octane and 1.65 g (11 mmol) of 5-methyl-2,3,4,5,6,7-hexahydro-1H-pyrrolo[3,4-c]pyridine. The suspension is concentrated at 70° C./20 mbar and the residue is stirred up with water. The precipitate is filtered off with suction, washed with water and dried at 100° C. in vacuo.

Yield: 3.7 g (88% of theory) of 6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid; melting point: 224°–226° C. (with decomposition). $^1$H-NMR (CDCl$_3$): $\delta$ about 8.68 ppm 2 s (1 H) (the splitting of this signal indicates 2 rotamers).

EXAMPLE 2

Under conditions corresponding to those in Example 1, (−)-6,7,8-trifluoro-1-(cis-2-fluorocyclopropyl)-1,4-dihydro-4-oxo-3-quinolinecarboxylic acid is used to obtain (−)-6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid, $[\alpha]_D^{26}$: −18° (c=0.5, DMF), melting point: 238°–240° C. (with decomposition).

EXAMPLE 3

Under conditions corresponding to those in Example 1, (+)-6,7,8-trifluoro-1-(cis-2-fluorocyclopropyl)-1,4-dihydro-4-oxo-3-quinolinecarboxylic acid is used to obtain (+)-6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid, $[\alpha]_D^{26}$: +18° (c=0.5, DMF), melting point: 240°–242° C. (with decomposition).

EXAMPLE 4

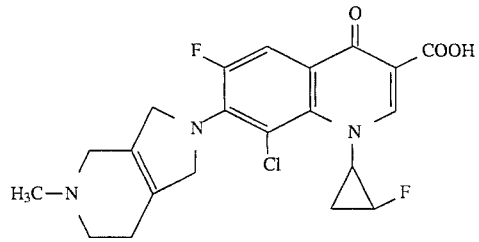

In analogy with Example 1, reaction takes place with 8-chloro-6,7-difluoro-1-(cis-2-fluorocyclopropyl)-1,4-dihydro-4-oxo-3-quinolinecarboxylic acid to form 8-chloro-6-fluoro-1-(cis-2-fluorocyclopropyl)-1,4-dihydro-7-(5-methyl-2,3,4,5,6,7-hexahydro-1H-pyrrolo[3,4-c]-pyridin-2-yl)-4-oxo-3-quinolinecarboxylic acid with a melting point of 204°–206° C. (with decomposition). $^1$H-NMR (CF$_3$COOD): $\delta$ about 9.3 ppm 2 s (1 H) (the splitting of this signal indicates 2 rotamers).

EXAMPLE 5

In analogy with Example 1, reaction takes place with 6,7-difluoro-1-(cis-2-fluorocyclopropyl)-1,4-dihydro-4-oxo-3-quinolinecarboxylic acid to form 6-fluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid.

EXAMPLE 6

301 mg (1 mmol) of 6-chloro-7-fluoro-1-(cis-2-fluorocyclopropyl)-1,4-dihydro-4-oxo-1,8-naphthyridone-3-carboxylic acid are initially introduced, at room temperature, in 3 ml of acetonitrile, 320 mg (2.1 mmol) of 5-methyl-2,3,4,5,6,7-hexahydro-1H-pyrrolo[3,4-c]-pyridine are added, and the mixture is stirred at room temperature for 6 hours. The insoluble material is filtered off with suction, washed with acetonitrile, taken up in 4 ml of warm 1N hydrochloric acid, and filtered through a sintered-glass filter. 6-chloro-1-(cis-2-fluorocyclopropyl)-1,4-dihydro-7-(5-methyl-2,3,4,5,6,7-hexahydro-1H-pyrrolo-[3,4-c]pyridin-2-yl)-4-oxo-1,8-naphthyridone-3-carboxylic acid hydrochloride is isolated from the filtrate once it has been concentrated and treated with ethanol.

EXAMPLE 7

In analogy with Example 1, reaction takes place with 8-chloro-6,7-difluoro-1-(trans-2-fluorocyclopropyl)-1,4-dihydro-4-oxo-3-quinolinecarboxylic acid to form 8-chloro-6-fluoro-1-(trans-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid with a melting point of 219°–221° C. (with decomposition).

EXAMPLE 8

In analogy with Example 1, reaction takes place with 5,6,7,8-tetrafluoro-1-(trans-2-fluorocyclopropyl)-1,4-dihydro-4-oxo-3-quinolinecarboxylic acid to form 5,6,8-trifluoro-1-(trans-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid.

EXAMPLE 9

In analogy with Example 1, reaction takes place with 8-bromo-6,7-difluoro-1-(trans-2-fluorocyclopropyl)-1,4-dihydro-4-oxo-3-quinolinecarboxylic acid to form 8-bromo-6-fluoro-1-(trans-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid with a melting point of 213°–215° C. (with decomposition).

EXAMPLE 10

301 mg (1 mmol) of 7-chloro-6-fluoro-1-(cis-2-fluorocyclopropyl)-1,4-dihydro-4-oxo-1, 8-naphthyridone-3-carboxylic acid are initially introduced at room temperature in 8 ml of acetonitrile, 320 mg (2.1 mmol) of 5-methyl-2,3,4,5,6,7-hexahydro-1H-pyrrolo[3,4-c]pyridine are then added, and the mixture is stirred at room temperature for 6 hours. The insoluble material is filtered off with suction and washed with acetonitrile, and 296 mg (74% of theory) of 6-fluoro-1-(cis-2-fluorocyclopropyl)-1,4-dihydro-7-(5-methyl-2,3,4,5,6,7-hexahydro-1H-pyrrolo[3,4-c]-pyridin-2-yl)-4-oxo-1, 8-naphthyridone-3-carboxylic acid are obtained with a melting point of 254°–257° C. (with decomposition). This is taken up in 4 ml of warm 1N hydrochloric acid and filtered through a sintered-glass filter. 6-Fluoro-1-(cis-2-fluorocyclopropyl)-1,4-dihydro-7-(5-methyl-2,3,4,5,6,7-hexahydro-1H-pyrrolo[3,4-c]-pyridin-2-yl)-4-oxo-1,8-naphthyridone-3-carboxylic acid hydrochloride is isolated from the filtrate once it has been concentrated and treated with ethanol.

Yield: 219 mg (50% of theory), melting point: 321°–325° C. (with decomposition).

We claim:
1. A compound of the formula

$$\text{(I)}$$

in which
$R^1$ represents hydrogen, $C_1$–$C_3$-alkyl which is optionally substituted by hydroxyl, $C_1$–$C_4$-alkoxycarbonyl, acetyl which is optionally substituted by halogen, or (5-methyl-2-oxo-1,3-dioxol-4-yl)-methyl, $R^2$ represents hydrogen, alkyl, having from 1 to 3 carbon atoms, which is optionally substituted by hydroxyl, methoxy, amino, methylamino or dimethylamino, or represents (5-methyl-2-oxo-1,3-dioxol-4-yl)-methyl, acetoxymethyl or pivaloyloxymethyl, represents 0 or 1, $X^1$ represents halogen or nitro, $X^2$ represents hydrogen, halogen, amino or methyl, A represents N, C—H, C—F, C—Cl, C—Br, C—CF$_3$, C—OCH$_3$, C—OCHF$_2$, C—CH$_3$ or C—C≡CH, or its pharmaceutically utilizable hydrate or acid addition salt, alkali metal salt alkaline earth metal salt, silver salt or guanidinium salt of the underlying carboxylic acids.

2. A compound according to claim 1,
in which
$R^1$ represents hydrogen, methyl, ethyl, t-butoxycarbonyl, acetyl, trifluoroacetyl or trichloroacetyl, $R^2$ represents hydrogen, n represents 0 or 1, $X^1$ represents chlorine or fluorine, $X^2$ represents hydrogen, fluorine, amino or methyl, A represents N, C—H, C—F, C—Cl, C—Br, C—CF$_3$, C—OCH$_3$, C—OCHF$_2$, C—CH$_3$ or C—C≡CH, or its pharmaceutically utilizable hydrate or acid addition salt, alkali metal salt alkaline earth metal salt, silver salt or guanidinium salt of the underlying carboxylic acids.

3. A compound according to claim 1,
in which
$R^1$ represents hydrogen or methyl, $R^2$ represents hydrogen, n represents 1, $X^1$ represents fluorine, $X^2$ represents hydrogen, fluorine or amino, A represents N, C—H, C—F, C—Cl, C—Br or C—OCH$_3$, or its pharmaceutically utilizable hydrate or acid addition salt, alkali metal salt, alkaline earth metal salt, silver salt or guanidinium salt of the underlying carboxylic acids.

4. A compound according to claim 1, which is enantiomerically pure.

5. A compound according to claim 1, wherein such compound is selected from the group consisting of
6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid;

(−)-6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl) -4-oxo-3-quinolinecarboxylic acid, ( +) -6,8-difluoro- 1- (cis-2-fluorocyclopropyl) -1,4-dihydro-7-(5-methyl-2,3,4,5,6,7-hexahydro-1H-pyrrolo[3,4-c]pyridin-2-yl)-4-oxo-3-quinolinecarboxylic acid and 8-chloro-6-fluoro-1- (cis-2-fluorocyclopropyl)-1,4-dihydro-7-(5-methyl-2,3,4,5,6,7-hexahydro-1H-pyrrolo[3,4-c ]pyridin-2-yl)-4-oxo-3-quinolinecarboxylic acid or an addition product thereof.

6. A racemic and enantiomerically pure compound selected from the group consisting of ethyl 5,6,7,8-tetrafluoro-1-(trans-2-fluoro-cyclopropyl)-1,4-dihydro-4-oxo-3-quinolinecarboxylate, 5,6,7,8-tetrafluoro-1-(trans-2-fluoro-cyclopropyl)-1,4-dihydro-4-oxo-3-quinolinecarboxylic acid, ethyl 5,6,7,8-tetrafluoro-1-(cis-2-fluoro-cyclopropyl)-4-dihydro-4-oxo-3-quinolinecarboxylate, 5,6,7,8-tetrafluoro-1-(cis-2-fluoro-cyclopropyl)-1,4-dihydro-4-oxo-3-quinolinecarboxylic acid, ethyl 8-bromo-6,7-difluoro-1-(trans-2-fluoro-cyclopropyl)-1,4-dihydro-4-oxo-3-quinolinecarboxylate, 8-bromo-6,7-difluoro-1-(trans-2-fluoro-cyclopropyl)-1,4-dihydro-4-oxo-3-quinolinecarboxylic acid, ethyl 8-bromo-6,7-difluoro-1-(cis-2-fluoro-cyclopropyl)-1,4-dihydro-4-oxo-3-quinolinecarboxylate, 8-bromo-6,7-difluoro-1-(cis-2-fluoro-cyclopropyl)-1,4-dihydro-4-oxo-3-quinolinecarboxylic acid, ethyl 6,7-difluoro-1-(trans-2-fluoro-cyclopropyl)-1,4-dihydro-8-methoxy-4-oxo-3-quinolinecarboxylate, 6,7-difluoro-1-(trans-2-fluoro-cyclopropyl)-1,4-dihydro-8-methoxy-4-oxo-3-quinolinecarboxylic acid, ethyl 6,7-difluoro-1-(cis-2-fluoro-cyclopropyl)-1,4-dihydro-8-methoxy-4-oxo-3-quinolinecarboxylate 6,7-difluoro-1-(cis-2-fluoro-cyclopropyl)-1,4-dihydro-8-methoxy-4-oxo-3-quinolinecarboxylic acid.

7. An antibacterial composition comprising an antibacterially effective amount of a compound or addition product thereof according to claim 1 and a diluent.

8. A composition according to claim 7 in the form of a tablet, capsule or ampule.

9. A composition according to claim 7, wherein the diluent comprises an animal feed stock.

10. A method of combating bacteria in a patient in need thereof which comprises administering to such patient an antibacterially effective amount of a compound or addition product thereof according to claim 1.

11. The method according to claim 10, wherein such compound is 6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid;

(−)-6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid, (+)-6,8-difluoro-1-(cis-2-fluorocyclopropyl)-1,4-dihydro-7-(5-methyl-2,3,4,5,6,7-hexahydro-1H-pyrrolo[3,4-c]pyridin-2-yl)-4-oxo-3-quinolinecarboxylic acid and 8-chloro-6-fluoro-1-(cis-2-fluorocyclopropyl)-1,4-dihydro-7-(5-methyl-2,3,4,5,6,7-hexahydro-1H-pyrrolo[3,4-c]-pyridin-2-yl)-4-oxo-3-quinolinecarboxylic acid or an addition product thereof.

12. A compound according to claim 1, wherein A is N.

* * * * *

UNITED STATES PATENT AND TRADEMARK OFFICE
CERTIFICATE OF CORRECTION

PATENT NO. : 5,545,642
DATED : August 13, 1996
INVENTOR(S) : Petersen, et al.

It is certified that error appears in the above-indentified patent and that said Letters Patent is hereby corrected as shown below:

| | |
|---|---|
| Title Page & Col. 1 line 5 | Delete " NAPHTHRIDONECARBOXYLIC " and substitute -- NAPHTHYRIDONECARBOXYLIC- |
| Title page, item [56], | FOREIGN PATENT DOCUMENTS: Delete " 04248851 " and substitute -- 0424851 -- |
| Col. 16, line 24 | Before " represents " insert -- n -- |
| Col. 17, line 19 | Before " 4 " insert -- 1, -- |

Signed and Sealed this

Eighteenth Day of March, 1997

Attest:

Attesting Officer

BRUCE LEHMAN

Commissioner of Patents and Trademarks